(12) United States Patent
Leyshon et al.

(10) Patent No.: US 6,583,300 B1
(45) Date of Patent: Jun. 24, 2003

(54) EPOXIDATION SYSTEM WITH FIXED BED REACTORS

(75) Inventors: David W. Leyshon, West Chester, PA (US); John C. Jubin, Jr., West Chester, PA (US); Richard J. Wolff, Pearland, TX (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/273,308

(22) Filed: Oct. 17, 2002

(51) Int. Cl.$^7$ .................... C07D 301/12; C07D 301/19

(52) U.S. Cl. ....................................... 549/529; 549/531

(58) Field of Search ................................. 549/529, 531

(56) References Cited

U.S. PATENT DOCUMENTS

| | | | |
|---|---|---|---|
| 3,351,635 A | 11/1967 | Kollar | 260/348.5 |
| 5,849,937 A | 12/1998 | Jubin et al. | 549/529 |
| 6,114,552 A | 9/2000 | Han et al. | 549/529 |
| 6,365,761 B1 | 4/2002 | Derks et al. | 549/529 |
| 6,383,966 B1 | 5/2002 | Han et al. | 502/63 |

*Primary Examiner*—Ba K. Trinh
(74) *Attorney, Agent, or Firm*—William C. Long

(57) ABSTRACT

A process for the production of an oxirane compound by reaction of an olefin with a hydroperoxide reactant in the presence of a solid epoxidation catalyst, wherein the olefin and hydroperoxide reactants are first reacted in it least two fixed bed reactors packed with fresh catalyst, olefin being fed serially to said reactors and hydroperoxide reactant being fed in parallel to said reactors and thereafter the reactor effluent from the last of said reactors is passed to as least one further fixed bed reactor packed with epoxidation catalyst which has been at least partially deactivated.

4 Claims, 1 Drawing Sheet

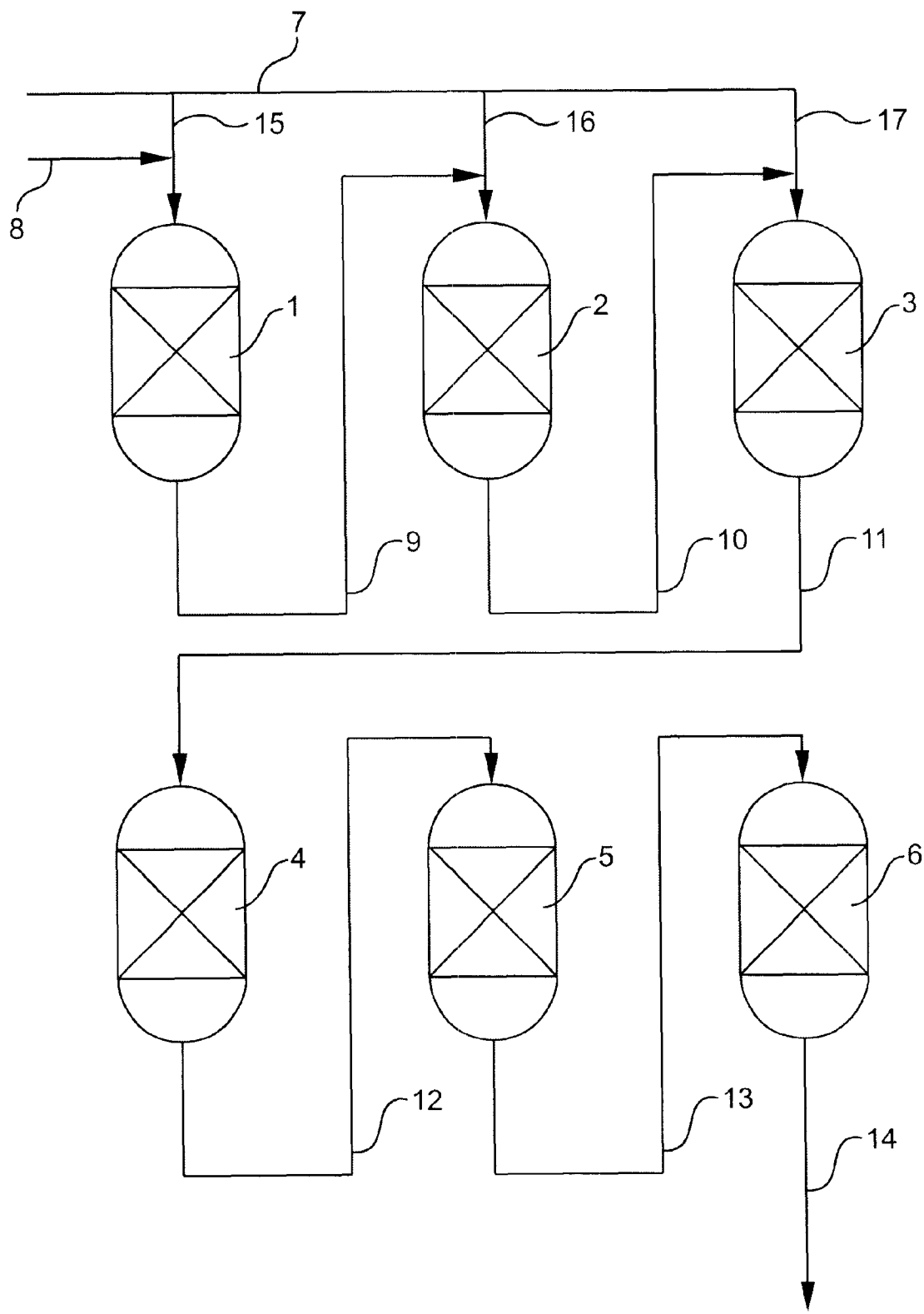

EPOXIDATION SYSTEM WITH FIXED BED REACTORS

BACKGROUND OF THE INVENTION

1. Field of the Invention

The present invention relates an epoxidation reaction system which uses fixed bed reactors packed with solid epoxidation catalyst.

2. Description of the Prior Art

It is known to produce oxirane compounds such as propylene oxide by catalytic reaction of an olefin with an organic hydroperoxide. See, for example, basic U.S. Pat. No. 3,351,635.

In certain embodiments, fixed bed reactors packed with solid heterogeneous epoxidation catalyst are employed. See, for example, U.S. Pat. Nos. 5,849,937 and 6,365,761.

There are certain problems associated with fixed bed epoxidation systems. On the one hand, high concentrations of organic hydroperoxide reactant cause problems with heat removal and temperature control in the system. Catalyst deactivation rates are accelerated at high temperatures and by feed poisons. Also process selectivity is greatly improved at higher ratios of olefin to hydroperoxide.

However, where high olefin to hydroperoxide ratios are used it is necessary to recover and recirculate large amounts of olefin and this has an adverse effect on process economics.

In addition, it is important that hydroperoxide conversion be essentially complete both for economic and safety reasons.

The present invention provides an improved system and process for oxirane compound production using fixed bed reactors.

BRIEF DESCRIPTION

In accordance with the present invention, olefin and organic hydroperoxide are passed through two or more fixed bed reactors which are packed with fresh or high activity catalyst, the hydroperoxide being fed in parallel to the reactors and the olefin being fed in series. Thereafter, the reaction effluent from the last of the high activity catalyst reactors is fed through one or more additional fixed bed reactors packed with used, partially deactivated catalyst to complete the reaction.

DESCRIPTION OF THE DRAWING

The accompanying drawing illustrates the invention.

DETAILED DESCRIPTION

Practice of the invention can be explained by reference to the accompanying drawing.

Referring to the drawing, reactors 1, 2 and 3 are fixed bed catalytic reactors packed with fresh high activity solid epoxidation catalyst while reactors 4, 5 and 6 are fixed bed catalytic reactors packed with partially deactivated solid epoxidation catalyst. By partially deactivated is meant catalyst having 1 to 10% of the activity of fresh catalyst.

An ethylbenzene oxidate stream comprised of ethylbenzene hydroperoxide is fed via line 7 in parallel to reactors 1, 2 and 3, about equal amounts of hydroperoxide being fed to each reactor. Propylene reactant is fed to reactor 1 via line 8, hydroperoxide via lines 7 and 15.

Reaction conditions are maintained in reactor 1 effective to react the predominance of the hydroperoxide fed thereto with propylene in to form propylene oxide.

A reactor effluent stream comprised of propylene oxide and unreacted propylene is passed via line 9 to reactor 2 where it is combined with hydroperoxide fed via lines 7 and 16 and in reactor 2 further reaction of propylene and the ethylbenzene hydroperoxide fed thereto takes place to form propylene oxide.

Effluent from reactor 2 passes via line 10 to reactor 3 where it is combined with hydroperoxide fed via line 7 and 17 and in reactor 3 further reaction of propylene and ethylbenzene hydroperoxide takes place with formation of propylene oxide.

Overall, there is a stoichiometric excess of propylene to hydroperoxide fed to the process and by feeding propylene in series to reactors 1, 2 and 3 while feeding the hydroperoxide in parallel to these reactors the reaction in each reactor is carried out at relatively high olefin to hydroperoxide ratios thus ensuring very high selectivity to propylene oxide. This, of course, requires the conventional use of mol ratios of propylene to hydroperoxide in excess of the stoichiometric ratios for the reaction.

The reaction effluent from reactor 3 is then passed through one or more fixed bed reactors packed with partially deactivated solid epoxidation catalyst. In the process described in the drawing three such reactors are employed, reactors 4, 5 and 6. Effluent from reactor 3 passes via line 11 to reactor 4, effluent from reactor 4 passes via line 12 to reactor 5, effluent from reactor 5 passes via line 13 to reactor 6 and effluent from reactor 6 passes via line 14 to conventional separation and recovery procedures.

Conversion of such hydroperoxide as is present in the effluent from reactor 3 takes place during passage through reactors 4, 5 and 6. It will be appreciated that although three reactors containing deactivated catalyst are illustrated, a greater or lesser number can be employed, usually one to five reactors.

In the process of this invention, an olefin is reacted with an organic hydroperoxide to form the corresponding epoxide. Although any ethylenically unsaturated organic compound could be used as the olefin, including branched, straight chain, cyclic, terminal or internal olefins, $C_2$–$C_6$ mono-olefins are particularly preferred. Examples of such mono-olefins include ethylene, propylene, n-butene, isobutylene, n-pentene, cyclohexene and the like. Ethylbenzene hydroperoxide, cumene hydroperoxide and tertiary butyl hydroperoxide are preferred hydroperoxides.

It is generally preferred to operate at an overall molar ratio of hydroperoxide:olefin in the range of from 1:2 to 1:30, more preferably, from 1:5 to 1:20.

The organic hydroperoxides usable as the active oxygen species in the epoxidation process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure:

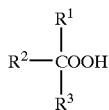

Wherein $R^1$, $R^2$ and $R^3$ are the same or different and are selected from the group consisting of hydrogen, $C_1$–$C_{10}$ alkyl (e.g. methyl, ethyl, t-butyl) and $C_6$–$C_{12}$ aryl (e.g., phenyl, alkyl substituted phenyl), subject to the proviso that not more than one of $R^1$, $R^2$, or $R^3$ is hydrogen. Exemplary organic hydroperoxides include t-butyl hydroperoxide, t-amyl hydroperoxide, cumene hydroperoxide, ethyl benzene hydroperoxide, cyclohexyl hydroperoxide, methyl cyclohexyl hydroperoxide, tetralin hydroperoxide, isobutyl benzene hydroperoxide, ethyl naphthalene hydroperoxide, and the like. Mixtures of organic hydroperoxides may also be employed.

The concentration of hydroperoxide in the feedstream introduced to the fixed bed reactors is not regarded as critical. Generally speaking, concentrations of from about 1 to 50 weight percent are suitable. The optimum concentration will depend upon the hydroperoxide and heterogeneous catalyst selected for use, the liquid phase olefin concentration, and the hydroperoxide: olefin molar ratio, among other factors.

The temperature, pressure, and liquid phase olefin concentration ranges selected for use with the present invention will vary somewhat depending upon the catalyst and active oxygen species employed. For example, the desirable temperature range is generally somewhat lower using a titanium silicalite catalyst than when a titania-on-silica catalyst is utilized.

Where the olefin is propylene and the hydroperoxide is ethyl benzene hydroperoxide, it is particularly desirable to control the temperature of reaction mixture in each reaction zone such that the temperature does not exceed 125° C. Controlling the temperature in this manner will help to maintain high reaction selectivity to propylene oxide while still permitting a high degree of hydroperoxide conversion in a particular reactor.

The catalyst employed in the present process may be any substance which is insoluble in the liquid phase of the epoxidation reaction mixture and capable of catalyzing the transformation of olefin to epoxide. Such catalysts are well-known in the art and may be of a crystalline (e.g., zeolitic) or amorphous character. Titanium-containing catalysts are particularly preferred for purposes of this invention.

Illustrative catalysts include titanium-containing molecular sieves comprising the class of zeolitic substances wherein titanium atoms are substituted for a portion of the silicon atoms in the lattice framework of a molecular sieve.

Particularly preferred titanium-containing molecular sieves include the molecular sieves commonly referred to as "TS-1" (having an MFI topology analogous to that of the ZSM-5 aluminosilicate zeolites; see U.S. Pat. No. 4,410,501).

Titanium-containing molecular sieves usable in the present process are sometimes variously referred to by workers in the field as "titanium silicalites", "titanosilicates", "titanium silicates", "silcon titanates" and the like.

Other suitable catalyst compositions are substances comprising an inorganic oxygen compound of silicon in chemical combination with an inorganic oxygen compound of titanium (e.g., an oxide or hydroxide of titanium). The inorganic oxygen compound of titanium is preferably combined with the oxygen compound so silicon in a high positive oxidation state, e.g., tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

Catalysts of this type are well-known in the art and are described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07,908 (Chem Abstracts 87:135000s), PCT Application No. WO 94/23834, German Patent Document No. 3,205648, and Castillo et al., *J. Catalysis* 161, pp. 524–529 (1996), the teachings of which are incorporated herein by reference in their entirety.

One type of such heterogeneous catalyst particularly suitable for use in the present invention is titania-on-silica (also sometimes referred to as "$TiO_2$/$SiO_2$"), which comprises titanium (titanium dioxide) supported on silica (silicon dioxide). The titania-on-silica may be in either silylated or nonsilylated form.

An especially useful catalyst is that prepared as described in U.S. Pat. Nos. 6,114,552 and 6,383,966 the disclosures of which are incorporated herein by reference.

The invention can be illustrated by the following example.

EXAMPLE

Ethylbenzene oxidate comprised by weight of 56.8% ethylbenzene, 35.0% ethylbenzene hydroperoxide and 8.2% others passes at the rate of about 592857 lbs/hr through line 7. Of this about 197600 lbs/hr is passed to reactor 1 via line 15, about 197600 lbs per hour is passed to reactor 2 via line 16 and about 197600 lbs/hr is passed to reactor 3 via line 17. The reactors are of about equal size and each is packed with solid epoxidation catalyst comprised of titanium on silica prepared in accordance with the procedure of Example 1 of U.S. Pat. No. 6,114,552.

A propylene feed stream comprised by weight of 90.0% propylene, 9.9% propane, and 0.1% others is passed at the rate of about 420548 lbs/hr via line 8 to reactor 1. The overall mol ratio of propylene introduced via line 8 to hydroperoxide introduced via line 7 is about 6:1.

In reactor 1 the mixture of propylene and ethylbenzene hydroperoxide enters the epoxidation catalyst bed at 68° C. and 1000 psig effective to form propylene oxide.

Reaction effluent comprised by weight of 58.0% propylene, 4.6% propylene oxide, 10.8% methyl benzyl alcohol, 18.2% ethylbenzene, 8.4% others passes via line 9 and is introduced to reactor 2 with the ethylbenzene hydroperoxide stream from lines 7 and 16.

In reactor 2 the feed components enter the epoxidation catalyst bed at 63° C. and 1000 psig effective to form propylene oxide. The reaction effluent passes from reactor 2 via line 10 and is introduced to reactor 3 with the ethylbenzene stream from lines 7 and 17. The composition by weight of the effluent from reactor 2 is 41.5% propylene, 6.9% propylene oxide, 16.3% methyl benzyl alcohol, 27.5% ethylbenzene, 0.4 % ethylbenzene hydroperoxide and 7.4% others.

In reactor 3 the feed components contact the epoxidation catalyst at 73° C. and 1000 psig effective to form propylene oxide. The reaction effluent from reactor 3 comprises by weight 31.4 % propylene, 8.3% propylene oxide, 19.6% methyl benzyl alcohol, 33.2% ethylbenzene, 0.5% ethylbenzene hydroperoxide and 7.0% others and passes at the rate of 1013000 lbs/hr to reactor 4.

Each of reactors 4, 5 and 6 is packed with catalyst prepared as the catalyst in reactors 1, 2 and 3, but which has been deactivated by use in the propylene oxide production such that the activity is less than 10% of the original fresh catalyst activity.

The reaction mixture from reactor 3 passes in series through reactors 4, 5 and 6 as shown, conditions in each of reactors 4, 5 and 6 being maintained at 112° C. and 1000 psig. Essentially complete conversion of the ethylbenzene hydroperoxide takes place during passage through reactors 4, 5 and 6 and a final reaction effluent is passed via line 14 at the rate of 1013000 lbs/hr for conventional separation and recovery. The composition by weight of this stream is 31.3% propylene, 4.1% propane, 8.4% propylene oxide, 19.8% methyl benzyl alcohol, 33.2% ethylbenzene and 3.2% others. The hydroperoxide content is less than 0.1 wt %.

Among the advantages which result from practice of the invention are reduced catalyst bed pressure drop due to lower olefin flow, reduced olefin recycle rate, increased catalyst life, high selectivity due to low hydroperoxide concentrations, simpler equipment and operation, and minimal downstream catalyst bed deactivation.

We claim:

1. In a process for the production of an oxirane compound by reaction of an olefin with a hydroperoxide reactant in the presence of a solid epoxidation catalyst, the improvement wherein the olefin and hydroperoxide reactants are first reacted in at least two fixed bed reactors packed with fresh catalyst, olefin being fed serially to said reactors and hydroperoxide reactant being fed in parallel to said reactors and thereafter passing the reactor effluent from the last of said reactors to at least one further fixed bed reactor packed with epoxidation catalyst which has been at least partially deactivated.

2. The process of claim 1 wherein said olefin is propylene.

3. The process of claim 1 wherein said hydroperoxide is ethyl benzene hydroperoxide.

4. The process of claim 1 wherein said at least one further fixed bed reactor is packed with catalyst having less than 10% of the activity of fresh catalyst.

* * * * *